United States Patent [19]

Oppawsky

[11] Patent Number: 5,198,678
[45] Date of Patent: Mar. 30, 1993

[54] DENTAL PHOTOPOLYMERIZATION DEVICE

[75] Inventor: Steffen Oppawsky, Bad Homburg, Fed. Rep. of Germany

[73] Assignee: Heraeus Kulzer GmbH, Wehrheim/TS, Fed. Rep. of Germany

[21] Appl. No.: 754,585

[22] Filed: Sep. 4, 1991

[30] Foreign Application Priority Data

Sep. 8, 1990 [DE] Fed. Rep. of Germany ....... 4028566

[51] Int. Cl.$^5$ .............................................. G21K 5/08
[52] U.S. Cl. ........................ 250/455.11; 250/453.11; 250/504 R; 250/504 H
[58] Field of Search ............ 250/455.1, 453.1, 504 R, 250/504 H

[56] References Cited

U.S. PATENT DOCUMENTS

| | | | |
|---|---|---|---|
| 3,712,984 | 3/1971 | Lienhard | 250/86 |
| 4,127,898 | 11/1978 | Fischer | 365/146 |
| 4,538,070 | 8/1985 | Herold et al. | 250/455.11 |
| 4,839,521 | 6/1989 | Oppawsky | 250/453.1 |

FOREIGN PATENT DOCUMENTS 3411996 10/1985 Fed. Rep. of Germany .

OTHER PUBLICATIONS

WPI Abstract of DE 3411996; Heraeus Kulzer Brochure No. 201288/D185 Skengl. "High Efficiency Hand-Held Light Unit".

*Primary Examiner*—Jack I. Berman
*Attorney, Agent, or Firm*—Frishauf, Holtz, Goodman & Woodward

[57] ABSTRACT

Polymerization devices having an irradiation space in an irradiation chamber, the space being accessible via at least one pivotable or displaceable wall, and having a light conductor and a radiation source unit, wherein the light conductor feeds the radiation from the radiation source into the irradiation space of the irradiation chamber and forms a releasable connection between the irradiation chamber and the radiation source unit, are known. To create a polymerization device that makes it possible to operate an irradiation chamber for curing plastic dental parts by means of a hand-held polymerization unit, with the capability of easy conversion from a hand-held polymerization unit to a stationary polymerization device, the radiation source unit is a hand-held polymerization unit, which is retained by its housing part on a first support, disposed on a support plate of a support frame; the light conductor is guided in a second support of the support plate; and the irradiation chamber is supported on a part of the support frame.

13 Claims, 1 Drawing Sheet

DENTAL PHOTOPOLYMERIZATION DEVICE

Cross-reference to related U.S. patents, the disclosures of which are incorporated by reference:
U.S. Pat. No. 3,712,984, LEINHARD
U.S. Pat. No. 4,127,898, FISCHER
U.S. Pat. No. 4,839,521, OPPAWSKY

FIELD OF THE INVENTION

The present invention relates to a polymerization device for treating plastic dental parts, having an irradiation space in an irradiation chamber, the space being accessible via at least one pivotable or displaceable wall, and having a light conductor and a radiation source unit; the light conductor feeds the radiation from the radiation source into the irradiation space of the irradiation chamber and forms a releasable connection between the irradiation chamber and the radiation source unit.

BACKGROUND

A polymerization device of this type is known from the Kulzer brochure "Translux, Hochleistungshandlichtgerate für Praxis und Labor" (German version No. 155188/D 185 sk; English version: "Translux EC: High efficiency hand-held light unit"). One of the radiation source units shown is a tabletop unit that has a connection for a light conductor. The light conductor that can be connected to it is long and flexible and has a grip element by which the light conductor is guided about the patient's mouth by the dentist. A curved light exit end is attached to the front end of the grip element.

An irradiation chamber, of the kind known from German Patent 37 08 204, can also be attached to the connection for the light conductor. The irradiation chamber rests directly on the tabletop unit and is supported by the table. This polymerization device, comprising the tabletop unit and the irradiation chamber connected to it, is dependent on the availability of a tabletop unit as the radiation source unit.

Besides these tabletop units, hand-held polymerization units, the housings of which contain not only the grip element but also operation and display elements, along with the light source and the fan, and stationary polymerization units, which contain an irradiation chamber and are used predominantly in dental laboratories, are also in use. Dentists' offices, however, often have only hand-held polymerization units on hand for treating plastic dental elements; such units are used exclusively inside the patient's mouth.

THE INVENTION

It is accordingly the object of the present invention to create a polymerization device that makes it possible to operate an irradiation chamber for curing plastic dental elements by using a hand-held polymerization unit, and to assure easy conversion of such a hand-held polymerization unit to a stationary one.

Briefly, the radiation source unit is a hand-held polymerization unit, which is retained by its housing part on a first support, disposed on a support plate of a support frame; external sheathing of the light conductor is guided in a second support of the support plate; and the irradiation chamber is supported and optionally fixed on a part of the support frame.

By combining an irradiation chamber and a hand-held polymerization unit, which is achieved by means of the support frame, it is possible to use a hand-held polymerization unit as a stationary one, in combination with an irradiation chamber. Hand-held polymerization units suitable for such use are known from German Patent Disclosure Documents DE-OS 26 27 249 and DE-OS 22 01 308, or from German Patent 34 11 996. The hand-held polymerization units include a radiation source, a fan, and operation and display elements. A socket by which various light conductors can be secured to the hand-held polymerization unit is mounted on the front of the hand-held polymerization unit. The housing part of this kind of hand-held polymerization unit is fixed in a recess in the first support. The external sheathing of the light conductor is guided through an opening in the second support, is held securely and firmly, for instance by form-fitting engagement with this opening, and is fastened in the irradiation chamber. The irradiation chamber is supported on the support frame.

The polymerization device according to the invention enables fast, uncomplicated conversion and stable coupling of a hand-held polymerization unit to an irradiation chamber, so that even in dentists' offices in which only a hand-held polymerization unit is available, plastic dental elements can be irradiated, cured and tempered in stationary fashion.

An especially practical embodiment of the support frame provides that the first support is a platform-like part that has an opening for receiving the hand-held polymerization unit. The housing part of the hand-held polymerization unit can be inserted into this opening and held securely and firmly by form-fitting engagement with it.

In a simple embodiment of the support frame, the supports are fastened vertically to the support plate.

The support frame may comprise plastic, such as acrylic glass, or sheet aluminum.

To simplify converting a hand-held polymerization unit to a stationary unit, the first support is slit from the opening to the outside; this assures accurate adjustment when the hand-held polymerization unit is mounted on the light conductor of the irradiation chamber. This slit can also offer the advantage that the entire hand-held polymerization unit need not be removed through the opening; instead, it suffices to pull out the housing and to run the light conductor to the outside through the slit. This simplifies the assembly and disassembly of the hand-held polymerization unit and irradiation chamber.

With a view to ease of connection or disconnection, the external sheathing of the light conductor can be connected interlockingly to the irradiation chamber and/or the hand-held polymerization unit. This assures fixation of the relative position of the hand-held polymerization unit and the irradiation chamber, and assures that constant radiation conditions prevail for the plastic dental element to be treated.

Advantageously, the irradiation chamber rests on the side of the second support remote from the hand-held polymerization unit, and external sheathing of the light conductor, by its face end, firmly clamps the second support in place between it and the irradiation chamber, in the interlocked state of the light conductor. This assures a stable connection between the irradiation chamber, the support frame and the hand-held polymerization unit, so that the entire polymerization device is intrinsically stable. In another advantageous arrangement, the irradiation chamber along with the light conductor is fixed by resting on the second support from the side of this support remote from the hand-held polymerization unit.

Additionally, the irradiation chamber along with the externally sheathed light conductor can be secured to the support plate of the support frame. In particular, this prevents torsion of the irradiation chamber relative to the optical axis of the beam of light.

Simple clamping is effected by providing the base of the irradiation chamber with two lateral ribs that partly enclose the outer contour of the support plate.

To increase the stability of the polymerization device still further, it is practical to retain the hand-held polymerization unit in the first support in a manner fixed against relative rotation. This prevents the components of the polymerization device from changing position on their own, and thereby altering irradiation conditions in the irradiation chamber or impairing the polymerization process as a result of jarring caused by twisting of the hand-held polymerization unit in the support frame.

The use of the polymerization device is also simplified by the torsionally fixed arrangement, because the operating or display elements on the hand-held polymerization unit, for instance, are always located at the same place and do not have to be searched for first.

In the event that the hand-held polymerization unit has a protrusion on its housing serving for instance to receive a display element or a cable lead, the torsionally fixed arrangement can be attained by engagement of this protrusion with an existing slit in the first support, without requiring any special components for the purpose.

To make for the simplest possible use, it is practical to fix the hand-held polymerization unit in the support frame in such a way that an activation switch on the housing is located on a side remote from the support plate. This not only makes the switch easily accessible, but also assures that the switch is always located at the same place and thus is always easy for the dentist using the unit to find.

To make the construction of the support plate as simple as possible, this component is at the same time embodied as the base plate of the support frame.

To make the structural design simple, the polymerization device is embodied such that the axis of the light conductor extends approximately parallel to the support plate.

The device can be secured to a wall, for instance with the aid of holes located in the support plate, or can be used as a stand-alone unit, in which case the light conductor is aligned with its axis extending horizontally.

An exemplary embodiment of the invention will be described in detail below, in conjunction with the drawing.

DRAWING

Figure 1:
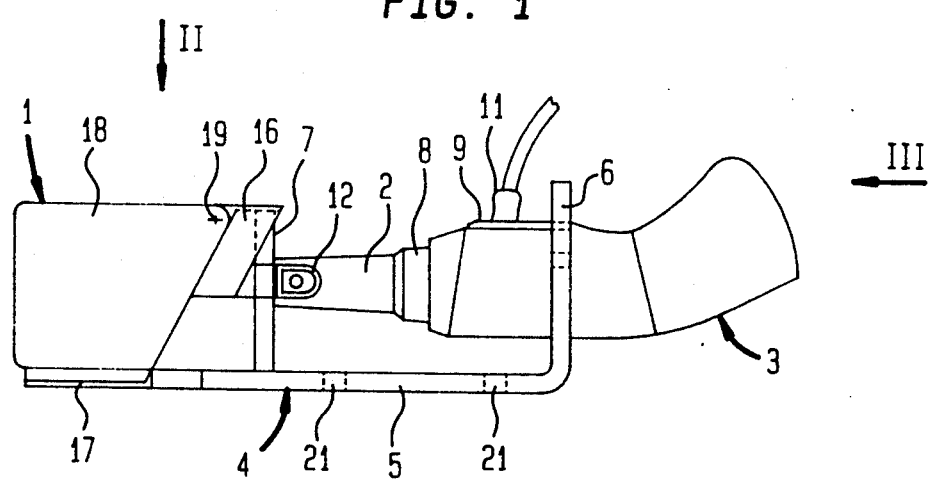
FIG. 1 is a side view of a polymerization device.
Figure 2:
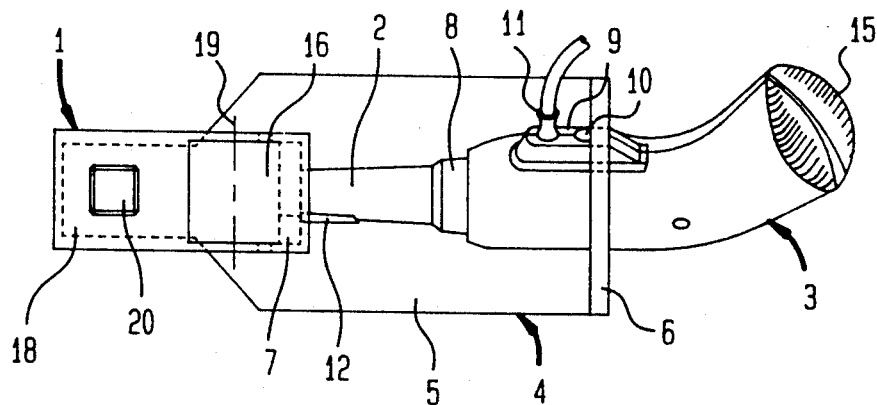
FIG. 2 is a plan view of the polymerization device, seen in the direction of the arrow II in FIG. 1.
Figure 3:
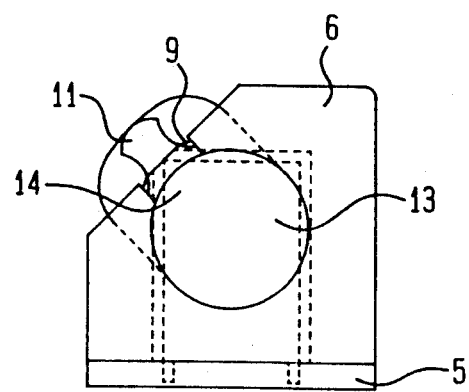
FIG. 3 is a side view of the polymerization device, seen in the direction of the arrow III in FIG. 1.

The polymerization device for treating plastic dental elements has an irradiation chamber 1 with a light conductor 2, a hand-held polymerization unit 3 serving as a radiation source unit, and a support frame 4, with the aid of which the other components of the polymerization device are fixed in their positions relative to one another.

The support frame 4 has a support plate 5, a first support 6 and a second support 7, both of which stand approximately vertically on the support plate 5 of the support frame 4.

The hand-held polymerization unit 3 has a housing, with the light source disposed in the front and the fan accommodated in the back. The back portion of the housing is bent somewhat at an angle, so as not to direct the air flow produced by the fan onto the arm of the doctor manipulating the hand-held polymerization unit. A socket 8 that serves to receive the light conductor 2 and its external sheathing is mounted on the front of the housing. A screw 10 for screwing the housing together and a trumpet-shaped cable guide 11 to protect against bending are mounted laterally on the front of the housing. An activation switch 12 is located on the socket 8 of the hand-held polymerization unit 3 in a position such that it can be actuated with the thumb if the socket 8 is held with the index finger.

The hand-held polymerization unit 3 is thrust with its socket part through an opening 13 of the first support 6 onto the external sheathing of the light conductor 2. The opening 13 corresponds to the cross section of the front part of the housing. The first support 6 also has a slit 14 extending through to the outside of the first support 6. The protrusion 9 located on the housing protrudes into this slit 14, so that the hand-held polymerization unit 3 is supported in a torsionally fixed manner, that is, in a manner fixed against relative rotation. The slit 14 is mounted at an angle of approximately 45° to the support plate 5, such that the air outlet opening 15 of the hand-held polymerization unit 3 points away from the body of the doctor using the polymerization device, and the activation switch 12 is located on a side remote from the support plate 5. The light conductor 2, located in the socket 8 along with its external sheathing, protrudes through an opening in the second support 7.

The irradiation chamber 1, which has an opening on one side for receiving the light conductor 2 and its external sheathing, is pressed by this opening onto the end of the light conductor 2 and its external sheathing; the external sheathing has an encompassing bead on one end, which locks into place in the opening of the irradiation chamber 1. A fixed housing part 16 of the irradiation chamber 1 then rests on the second support 7. The base of the irradiation chamber 1 has two lateral ribs on the bottom that partly enclose the outer contour of the support plate 5.

To make it possible to equip the irradiation chamber 1 appropriately, the upper housing portion 18 of the irradiation chamber 1 is supported on a pivot shaft 19. The pivot shaft 19 is located near the part of the fixed housing portion 16 that rests on the second support 7. A window 20 by which the polymerization process can be observed is let into the top of the upper housing portion 18.

The openings in the first support 6 and second support 7 are mounted such that the axis of the light conductor 2 extends parallel to the support plate 5.

The entire support frame 4 is made from acrylic glass.

Holes 21 by which the polymerization device can be secured to a table or a wall are located in the support plate 5.

Various changes and modifications may be made, and features described in connection with the embodiment may be used in any combination, within the scope of the inventive concept.

I claim:

1. A photopolymerization device for treating plastic dental parts, having an irradiation space in an irradiation chamber (1), the space being accessible via at least one pivotable or displaceable wall, and having a light conductor (2) and a radiation source unit (3), wherein the light conductor (2) feeds the radiation from the radiation source into the irradiation space of the irradiation chamber (1) and forms a releasable connection between the irradiation chamber and the radiation source unit, wherein said radiation source unit is a hand-held polymerization unit (3), having a housing part;

said irradiation chamber (1) is coupled to a support frame (4) including a first support (6) and a second support (7), disposed on a support plate (5) forming a part of said support frame (4); and said hand-held polymerization unit (3) and said support frame (4) are formed with matching shapes adapted for rapid yet form-fitting engagement with one another to provide said releasable connection, said connection being formed upon engagement of said housing part in said first support (6) and of said light conductor (2) in said second support (7), said connection assuring fixation of the relative position of the polymerization unit and the chamber to thereby assure constant radiation conditions in said chamber.

2. The polymerization device of claim 1, characterized in that
the first support (6) is a platform-like part that has an opening (13) for receiving the hand-held polymerization unit (3).

3. The polymerization device of claim 2, characterized in that
the first support (6) has a slit (14) extending all the way from the opening (13) through to the outside.

4. The polymerization device of claim 1, characterized in that
the light conductor (2) has external sheathing that is connected to at least one of the irradiation chamber (1) and the hand-held polymerization unit (3).

5. The polymerization device of claim 4, characterized in that
the second support (7) holds the external sheathing of the light conductor (2), and the irradiation chamber (1) rests on the second support (7).

6. The polymerization device of claim 1, characterized in that
the irradiation chamber (1) is fastened to the support plate (5).

7. The polymerization device of claim 1, characterized in that
the irradiation chamber (1) has ribs (17) on its underside that partly enclose the outer contour of the support plate (5).

8. The polymerization device of claim 1, characterized in that
the hand-held polymerization unit (3) is retained in the first support (6) in a manner fixed against relative rotation.

9. The polymerization device of claim 3, characterized in that
the hand-held polymerization unit (3) has a protrusion (9) that engages the slit (14).

10. The polymerization device of claim 1, characterized in that
the hand-held polymerization unit (3) has an activation switch (12), the hand-held polymerization unit (3) being fixed in the support frame (4) in such a way that the activation switch (12) is located on a side remote from the support plate (5).

11. The polymerization device of claim 1, characterized in that
the support plate (5) forms the base plate of the support frame (4).

12. The polymerization device of claim 1, characterized in that
the axis of the light conductor (2) extends parallel to the support plate (5).

13. The polymerization device of claim 12, characterized in that
the light conductor (2) extends with its axis aligned horizontally.

* * * * *